(12) United States Patent
Foley et al.

(10) Patent No.: US 8,523,914 B2
(45) Date of Patent: Sep. 3, 2013

(54) BONE ANCHOR WITH PREDETERMINED BREAK POINT AND REMOVAL FEATURES

(75) Inventors: Kevin T Foley, Germantown, TN (US); Thomas A Carls, Memphis, TN (US); Newt H Metcalf, Jr., Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 693 days.

(21) Appl. No.: 12/695,851

(22) Filed: Jan. 28, 2010

(65) Prior Publication Data

US 2011/0184471 A1 Jul. 28, 2011

(51) Int. Cl.
*A61B 17/70* (2006.01)

(52) U.S. Cl.
USPC .......................................... 606/265

(58) Field of Classification Search
USPC ........ 606/86 A, 264–279, 300–323, 325–329
See application file for complete search history.

(56) References Cited

U.S. PATENT DOCUMENTS

| | | | | |
|---|---|---|---|---|
| 1,269,971 | A * | 6/1918 | Smith | 411/393 |
| 4,763,644 | A * | 8/1988 | Webb | 606/267 |
| 5,019,078 | A * | 5/1991 | Perren et al. | 606/313 |
| 5,653,710 | A | 8/1997 | Harle | |
| 5,697,929 | A | 12/1997 | Mellinger | |
| 6,004,349 | A | 12/1999 | Jackson | |
| 6,039,738 | A * | 3/2000 | Sanders et al. | 606/86 A |
| 6,059,786 | A | 5/2000 | Jackson | |
| 6,102,912 | A | 8/2000 | Cazin | |
| 6,102,913 | A | 8/2000 | Jackson | |
| 6,179,841 | B1 | 1/2001 | Jackson | |
| 6,355,043 | B1 * | 3/2002 | Adam | 606/62 |
| 6,454,765 | B1 | 9/2002 | Leveen | |
| 6,454,768 | B1 | 9/2002 | Jackson | |
| 6,454,772 | B1 * | 9/2002 | Jackson | 606/306 |
| 6,699,251 | B1 * | 3/2004 | Venturini | 606/318 |
| 6,723,099 | B1 * | 4/2004 | Goshert | 606/329 |
| 6,730,089 | B2 | 5/2004 | Jackson | |
| 6,740,086 | B2 * | 5/2004 | Richelsoph | 606/60 |
| 6,875,215 | B2 * | 4/2005 | Taras et al. | 606/916 |
| 7,261,716 | B2 * | 8/2007 | Strobel et al. | 606/314 |
| 7,316,532 | B2 * | 1/2008 | Matthys-Mark | 411/5 |
| 7,927,360 | B2 * | 4/2011 | Pond et al. | 606/265 |
| 7,955,363 | B2 * | 6/2011 | Richelsoph | 606/305 |
| 8,262,662 | B2 * | 9/2012 | Beardsley et al. | 606/86 A |
| 2002/0068938 | A1 | 6/2002 | Jackson | |
| 2003/0040751 | A1 * | 2/2003 | Weil et al. | 606/73 |
| 2004/0039383 | A1 | 2/2004 | Jackson | |
| 2004/0162560 | A1 * | 8/2004 | Raynor et al. | 606/73 |
| 2004/0249381 | A1 * | 12/2004 | Weil et al. | 606/73 |
| 2005/0182410 | A1 * | 8/2005 | Jackson | 606/73 |

(Continued)

*Primary Examiner* — Mary Hoffman

(57) ABSTRACT

A bone anchor including a bone engaging portion, a tool engaging portion configured for engagement with an anchor removal tool, a head portion having a transverse base portion and two arm portions that together define a U-shaped channel, and a reduced strength portion extending between the tool engaging portion and the head portion and defining a region of reduced strength to provide a pre-defined fracture initiator or break zone. In another embodiment, the bone anchor includes a proximal head and a threaded shank having a plurality of thread turns adapted for anchoring to bone and extending along a threaded length that is at least twice the overall height of the proximal head, and a plurality of grooves circumferentially interrupting at least one of the thread turns along a proximal region of the threaded shank and sized and shaped for engagement with an anchor removal instrument.

28 Claims, 11 Drawing Sheets

(56) References Cited

U.S. PATENT DOCUMENTS

| | | |
|---|---|---|
| 2005/0251142 A1* | 11/2005 | Hoffmann et al. .............. 606/65 |
| 2005/0267477 A1 | 12/2005 | Jackson |
| 2006/0276789 A1 | 12/2006 | Jackson |
| 2008/0014042 A1 | 1/2008 | De France |
| 2008/0082103 A1* | 4/2008 | Hutton et al. .................. 606/73 |
| 2008/0119849 A1* | 5/2008 | Beardsley et al. .............. 606/61 |
| 2008/0119850 A1 | 5/2008 | Sicvol |
| 2008/0300638 A1* | 12/2008 | Beardsley et al. ............ 606/306 |

* cited by examiner

BONE ANCHOR WITH PREDETERMINED BREAK POINT AND REMOVAL FEATURES

FIELD OF THE INVENTION

The present invention relates generally to the field of bone anchors, and more particularly relates to bone anchors having a predetermined break point and/or removal features.

BACKGROUND

Various types of bone anchors are used to engage implants and other types of devices to bone. In the spinal field, bone screws are commonly used to attach plates, rods and other types of implants and devices to one or more vertebrae. Many existing bone screws include a threaded shank portion adapted for engagement in bone, and a head portion for coupling to an elongate member such as a spinal rod.

Breakage of bone screws in orthopedic applications is a somewhat common adverse event which may be caused, for example, by trauma, obesity, dynamic movement, non-unions or other events or actions that lead to screw fatigue failure. Bone screw breakage typically occurs below the head portion of the bone screw and adjacent the surface of the bone where the threaded shank portion has penetrated into the bone. Since the head portion of the bone screw normally includes the structural features that serve to drive the screw into bone, the process of extracting the threaded shank portion from the bone after the head portion has broken away from the remainder of the screw can be difficult and time consuming, and may require removal of a portion of the bone material adjacent the threaded shank portion which can lead to weakening of the structure of the bone.

Thus, there remains a need for an improved bone anchor having a predetermined break point and/or removal features. The present invention satisfies this need and provides other benefits and advantages in a novel and unobvious manner.

SUMMARY

The present invention relates generally to the field of bone anchors, and more particularly relates to bone anchors having a predetermined break point and/or removal features.

According to one aspect, a bone anchor is provided comprising a bone engaging portion having a longitudinal axis and adapted for anchoring to bone, a tool engaging portion extending axially from the bone engaging portion and sized and shaped for engagement with an anchor removal tool, a head portion having a transverse base portion and two arm portions extending axially therefrom to define a U-shaped channel having an upper opening defined between distal ends of the arm portions and intersecting the longitudinal axis and sized to axially receive an elongate member into the U-shaped channel, and a reduced strength portion extending between the tool engaging portion and the head portion and defining a region of reduced strength relative to adjacent portions of the tool engaging portion and the head portion to provide a pre-defined fracture initiator or break zone.

According to another aspect, a spinal stabilization system is provided comprising a first bone anchor according to the bone anchor embodiment described immediately above for anchoring to a first vertebra, a second bone anchor according to the bone anchor embodiment described immediately above for anchoring to a second vertebra, a flexible elongate member positioned through the upper openings and into the U-shaped channels of the first and second bone anchors with the flexible elongate member having sufficient flexibility relative to the reduced strength portions of the first and second bone anchors to avoid breakage of the first and second bone anchors along the pre-defined fracture initiator zones when the flexible elongate member is initially positioned into the U-shaped channels, a first closure member engaged with the arm portions of the first bone anchor to capture the flexible elongate member within the U-shaped channel of the first bone anchor, and a second closure member engaged with the arm portions of the second bone anchor to capture the flexible elongate member within the U-shaped channel of the second bone anchor.

According to another aspect, a bone anchor is provided comprising a threaded shank portion having a longitudinal axis and including external threads adapted for anchoring to bone, a tool engaging portion extending axially from the threaded shank portion and having a non-circular transverse cross section sized and shaped for engagement with an anchor removal tool, a head portion having a transverse base portion and two arm portions extending axially therefrom to define a U-shaped channel having an opening defined between distal ends of the arm portions and intersecting the longitudinal axis and sized to axially receive an elongate member into the U-shaped channel with the two arm portions defining internal threads, and a reduced strength portion extending between the tool engaging portion and the head portion and having a reduced cross section relative to adjacent portions of the tool engaging portion and the head portion to define a region of reduced strength relative to the adjacent portions of the tool engaging portion and the head portion to provide a pre-defined fracture initiator or break zone and wherein the transverse base portion of the head portion is integrally joined with the tool engaging portion by the reduced strength portion to provide the head portion and the tool engaging portion as a single unitary piece, and a set screw engaged with the internal threads of the axial arm portions to capture the elongate member within the U-shaped channel.

According to another aspect, a bone anchor is provided comprising a proximal head having an overall height, and a threaded shank having a longitudinal axis and including a plurality of thread turns adapted for anchoring to bone and extending along a threaded length of the threaded shank with the threaded length being at least twice the overall height of the proximal head, and wherein the threaded shank includes a plurality of grooves extending axially along the longitudinal axis and circumferentially interrupting at least one of the thread turns along a proximal region of the threaded shank with the plurality of grooves sized and shaped for engagement with an anchor removal instrument.

Further embodiments, forms, features, aspects, benefits, objects and advantages of the present invention will become apparent from the detailed description and figures provided herewith.

DESCRIPTION OF THE ILLUSTRATED EMBODIMENTS

Figure 1:
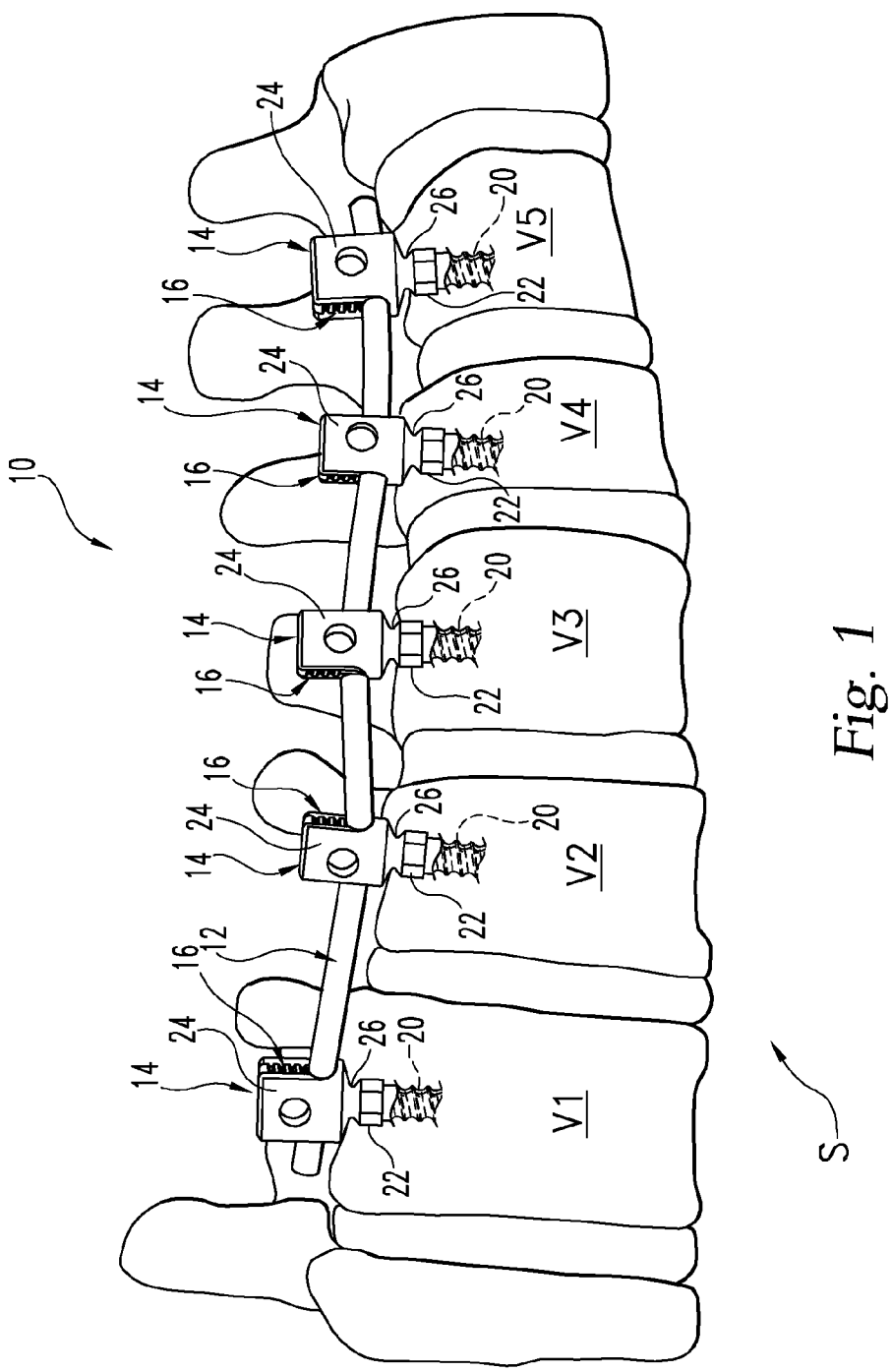
FIG. 1 is a postero-lateral perspective view of a spinal stabilization system according to one form of the present invention, as attached to a posterior aspect of the spinal column.

For the purposes of promoting an understanding of the principles of the invention, reference will now be made to the embodiments illustrated in the drawings and specific language will be used to describe the same. It will nevertheless be understood that no limitation on the scope of the invention is intended. Any alterations and further modifications in the illustrated devices and described methods and further applications of the principles of the invention as disclosed herein are contemplated as would normally occur to one skilled in the art to which the invention relates.

Referring to FIG. 1, shown therein is one form of a spinal stabilization system 10 for stabilizing at least a portion of the spinal column. The stabilization system 10 is shown attached to a spinal motion segment S that extends across a plurality of vertebrae V1, V2, V3, V4 and V5. The stabilization system 10 generally includes an elongate support member 12 secured to the spinal motion segment S via a plurality of bone anchors 14, with each bone anchor 14 engaged to a respective one of the vertebrae V1-V5, and more specifically to the pedicle regions of the vertebrae V1-V5. However, it should be understood that the bone anchors 14 may be engaged to any number of vertebrae, and that the stabilization system 10 may extend across a spinal motion segment having only two vertebrae or three or more vertebrae. It should also be understood that the bone anchors 14 may be engaged to other portions or regions of the vertebrae. A closure member or plug 16 is engaged with each of the bone anchors 14 to capture the elongate support member 12 within an opening in the bone anchor 14. In the illustrated embodiment, the elongate support member 12 is configured as a spinal rod having a circular outer cross section. However, it should be understood that other types and configurations of elongate support members and other cross-sectional shapes and configurations of spinal rods are also contemplated as falling within the scope of the present invention.

It should further be understood that the stabilization system 10 may be utilized in all regions of the spine, including the cervical, thoracic, lumbar, lumbo-sacral and sacral regions of the spine column. It is further contemplated that two or more stabilization systems 10 may be utilized simultaneously along the same spinal motion segment such as, for example, two stabilization systems bi-laterally anchored to a spinal motion segment. Additionally, although the stabilization system 10 is illustrated as being engaged to a posterior aspect of the spinal motion segment S, the stabilization system 10 may alternatively be applied in other surgical approaches and combinations of surgical approaches to the spinal motion segment S such that one or more of the stabilization systems 10 are engaged with the anterior, antero-lateral, lateral and/or postero-lateral aspects of the spinal motion segment S. It should likewise be understood that the bone anchors 14 may be attached to bone structures other than vertebral bodies such as, for example, bones associated with the arm, leg or bones associated with other areas or regions of the body.

In one embodiment, the stabilization system 10 allows at least small degrees of dynamic spinal motion in the spinal motion segment S. In a specific embodiment, the elongate support member 12 of the stabilization system 10 is flexible and/or flexibly attached between the adjacent bone anchors 14 to provide a degree of dynamic spinal motion in the spinal motion segment S. Additionally, it should be understood that the stabilization system 10 can be used in association with fusion or non-fusion treatment of the spine.

In one embodiment, the elongate support member 12 is formed of a first material, and the bone anchors 14 are formed of a second material different from the first material. In one specific embodiment, the elongate member 12 is formed of a flexible, non-rigid material such as, for example, a polymeric or PEEK material, one or more superelastic metals or alloys such as, for example, nitinol, a composite material, or other flexible, non-rigid materials that would occur to one of ordinary skill in the art. In another specific embodiment, the elongate member 12 is a flexible tether formed of one or polymers such as, for example, polyester or polyethylene, or a resorbable synthetic material such as, for example, suture material or polylactic acid. One example of a spinal stabilization system utilizing a flexible tether is disclosed in U.S. Pat. No. 7,018,379 to Drewry et al., the contents of which are hereby incorporated by reference in their entirety. It is further contemplated that the elongate member 12 may be provided with elastic resilience such that when bent, the elongate member 12 will tend to return toward its pre-bent state, and when tensioned, the elongate member 12 will tend to return toward its pre-tensioned state. The bone anchors 14 and the closure members 16 may be formed from any suitable biocompatible material including, for example, titanium, a titanium alloy, stainless steel, metallic alloys, or other materials known to those of skill in the art that possess the mechanical and biocompatible properties suitable for implantation within the body and which are biocompatible with the elongate member 12.

Figure 2:
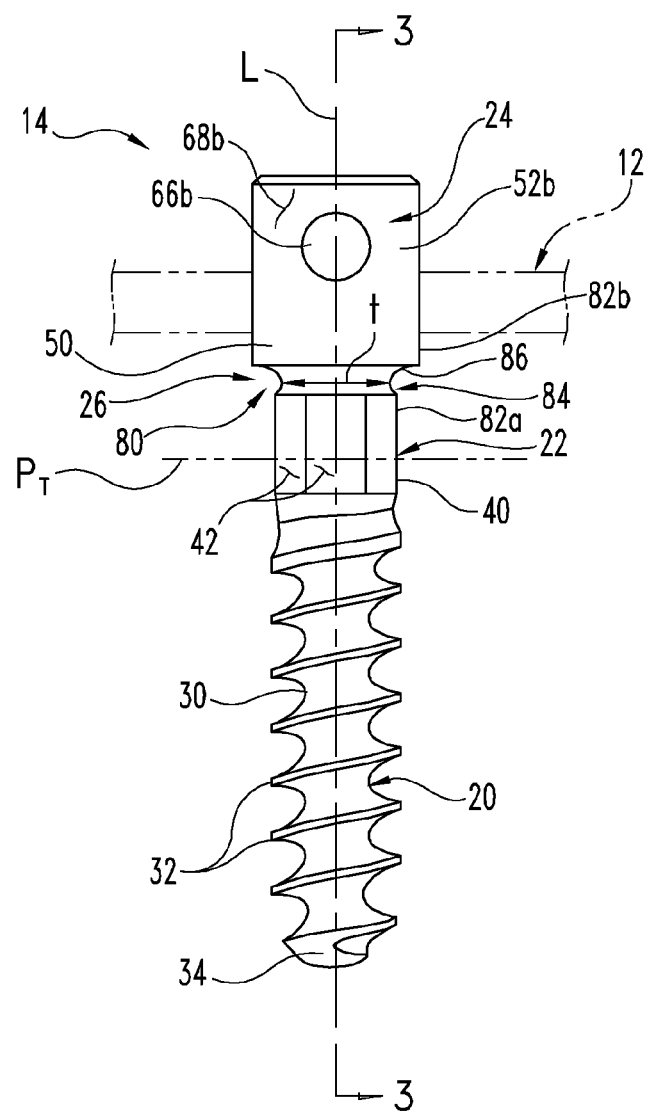
FIG. 2 is an elevational side view of one embodiment of a bone anchor for use in association with the spinal stabilization system illustrated in FIG. 1.
Figures 3, 4:
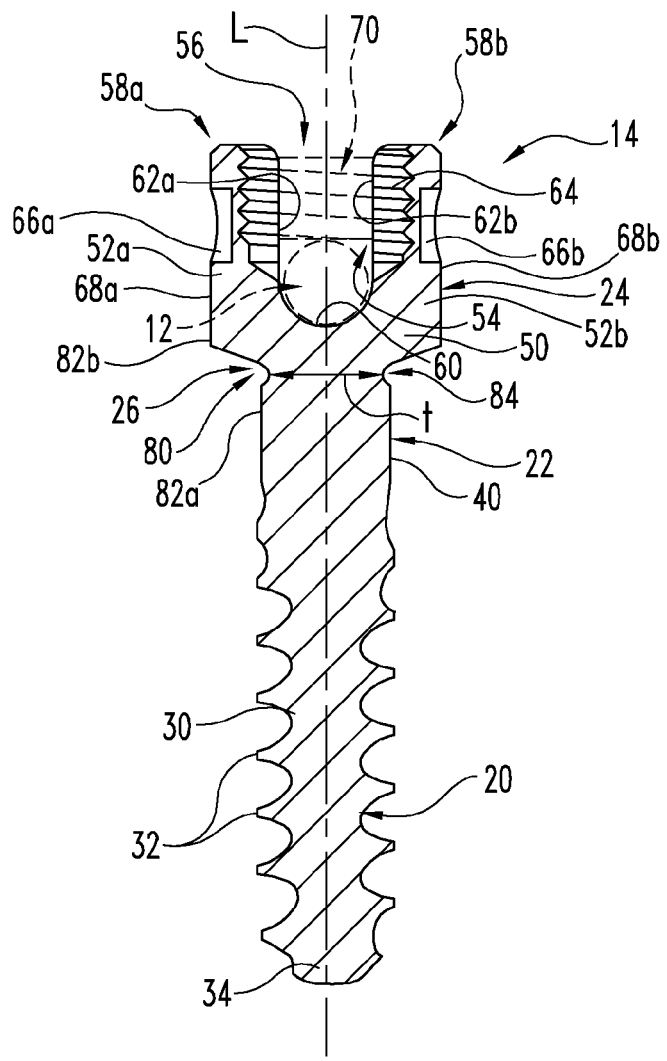
FIG. 3 is a cross-sectional view of the bone anchor illustrated in FIG. 2, as taken along line 3-3 of FIG. 2.
FIG. 4 is a side perspective view of one embodiment of a locking member for use in association with the spinal stabilization system illustrated in FIG. 1.

Referring to FIGS. 2 and 3, shown therein is a bone anchor 14 according to one form of the present invention. In the illustrated embodiment, the bone anchor 14 generally includes a bone engaging portion 20 adapted for anchoring to bone, a tool engaging portion 22 extending axially from a proximal end of the bone engaging portion 20 and sized and shaped for engagement with a bone anchor removal tool, a head portion 24 configured to receive the elongate support member 12, and a reduced strength portion 26 extending between the tool engaging portion 22 and the head portion 24.

In the illustrated embodiment, the bone anchor 14 is configured as a bone screw with the bone engaging portion 20 comprising a threaded shank 30 having a length extending along a longitudinal axis L and including external threads 32 configured for anchoring in bone. The threaded shank 30 includes a distal end portion 34 that is configured to penetrate bone. In one embodiment, the distal end portion 34 may be tapered or pointed to facilitate entry into bone. However, in other embodiments, the distal end portion 34 may define a blunt or rounded end. In further embodiments, the distal end portion 34 or other portions of the threaded shank 30 may be provided with one or more cutting edges or flutes (not shown) extending across one or more turns of the external threads 32 to provide the bone anchor 14 with self-cutting or self-tapping capabilities. In still other embodiments, the bone anchor 14 may be provided with an axial passage (not shown) extending from the head portion 24 and partially or entirely through the threaded shank 30 to define a cannulation opening. Although the illustrated embodiment of the bone anchor 14 is configured as a bone screw with the bone engaging portion 20 defining external threads 32, it should be understood that the bone engaging portion 20 may alternatively be provided with other bone engaging structures such as, for example, barbs, ratchets, spikes, pivoting gulls or other types of projections configured to engage bony tissue. In still other embodiments, the bone engaging portion 20 may be provided in the form of a spinal hook configured to engage and wrap about a portion of a vertebral body.

Figure 7:
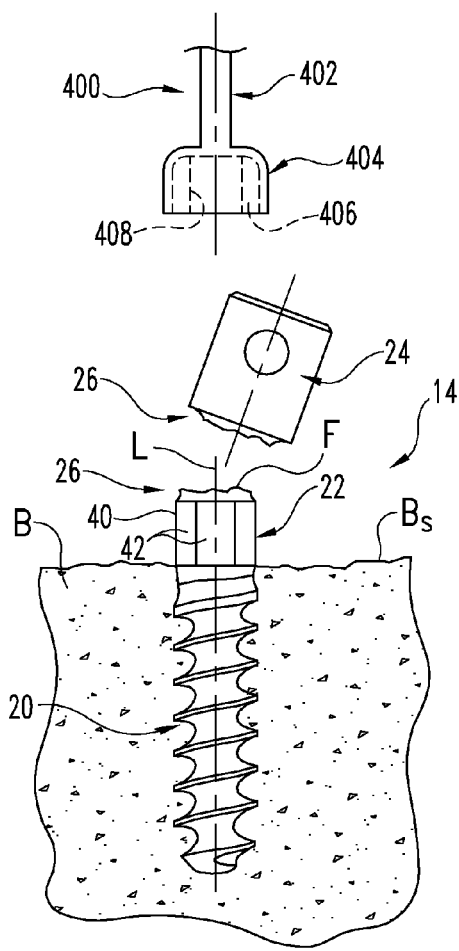
FIG. 7 is a lateral view of the bone anchor illustrated in FIG. 3 with the bone engaging portion anchored within vertebral bone and with the head portion broken away from the bone engaging portion, and also illustrating one embodiment of a removal tool for removal of the bone engaging portion of the bone anchor from the bone.

In the illustrated embodiment, the tool engaging portion 22 of the bone anchor 14 is configured for engagement with a bone anchor removal tool such as, for example, the bone anchor removal tool 400 illustrated in FIG. 7. As discussed below, upon removal or breakage of the head portion 24 from the remainder of the bone anchor 14, at least a portion of the tool engaging portion 22 will remain exposed above the outer bone surface $B_S$ to provide an accessible structure for engagement by the bone anchor removal tool 400 to facilitate removal of the bone engaging portion 20 from the bone B.

In one embodiment, the tool engaging portion 22 has a non-circular outer transverse cross section taken along a transverse plane $P_T$ arranged generally perpendicular to the longitudinal axis L. The non-circular outer transverse cross section is defined by an outer periphery 40 of the tool engaging portion 22. In a specific embodiment, the outer periphery 40 of the tool engaging portion 22 includes a plurality of flattened surfaces 42 that provide the tool engaging portion 22 with the non-circular outer transverse cross section. In the illustrated embodiment, the outer periphery 40 of the tool engaging portion 22 has a polygonal shape, and more particularly a hexagonal shape, to provide the tool engaging portion 22 with the non-circular outer transverse cross section. However, it should be understood that other shapes and configurations of the tool engaging portion 22 are also contemplated as falling within the scope of the present invention. For example, in other embodiments, the tool engaging portion 22 may be provided with one or more transverse openings or channels sized and configured to receive a corresponding end portion of a bone anchor removal tool to facilitate removal of the bone engaging portion 20 from the bone, or may alternatively be provided with one or more transverse projections or tongues sized and configured for receipt within a corresponding opening or channel formed in a bone anchor removal tool to facilitate removal of the bone engaging portion 20 from the bone.

In the illustrated embodiment, the head portion 24 of the bone anchor 14 is tulip-shaped and includes a transverse base portion 50 and two arm portions 52a, 52b extending axially from the transverse base portion 50 generally along the longitudinal axis and laterally spaced apart from one another to define a generally U-shaped channel 54 having an upper opening 56 defined between distal ends 58a, 58b of the arm portions 52a, 52b and intersecting the longitudinal axis L. The upper opening 56 is sized to axially receive the elongate member 12 into the U-shaped channel 54 in a direction along the longitudinal axis L in a top-loading manner. Additionally, the transverse base portion 50 may be provided with an arcuate or semi-circular lower bearing surface 60 extending between the opposing inner side surfaces 62a, 62b of the arm portions 52a, 52b and sized and shaped to matingly receive and engage the elongate member 12. Furthermore, in one embodiment, the transverse base portion 50 is integrally joined with the tool engaging portion 22 by the reduced strength portion 26 to provide the head portion 24 and the tool engaging portion 22 as a single unitary piece. In a further embodiment, the bone engaging portion 20, the tool engaging portion 22, the head portion 24, and the reduced strength portion 26 are all formed integral with one another to provide the entire bone anchor 14 as a single unitary piece. In an alternative embodiment, the bone anchor 14 may be configured as a poly-axial or multi-axial bone screw wherein the head portion 24 is pivotally attached to the remainder of the bone anchor 14, an example of which is disclosed in U.S. Pat. No. 5,879,350 to Sherman et al., the contents of which are hereby incorporated by reference in their entirety. In one such embodiment, the head portion 24 of the bone anchor may be provided with an at least partially spherical-shaped recess that is sized and shaped to receive an at least partially spherical-shaped projection attached to an upper end of the tool engaging portion 22 via the reduced strength portion 26.

Additionally, in the illustrated embodiment, each of the arm portions 52a, 52b define internal threads 64 formed along an axial length of the opposing inner surfaces 62a, 62b, and the arm portions 52a, 52b further define recesses or indentations 66a, 66b formed in the oppositely facing outer surfaces 68a, 68b and which are sized and shaped to receive distal end portions of an insertion tool, a compression/reduction instrument, and/or other instruments or tools configured to grasp, manipulate and/or drive the bone anchor 14 into bone tissue and/or to compress/reduce the elongate member 12 into the U-shaped channel 54 of the head portion 24.

As illustrated in FIG. 4, in one embodiment, the closure member 16 is configured as a set screw having a cylindrically-shaped set screw body 70 defining external threads 72 and a tool engaging recess or receptacle 74 configured to receive a distal end portion of a driving tool therein such as, for example, a screw driver. In the illustrated embodiment, the tool engaging recess 74 has a Torx-shaped configuration. However, other shapes and configurations of the tool engaging recess 74 are also contemplated such as, for example, a hexagonal-shaped configuration or other polygonal shapes and configurations. As should be appreciated, the set screw 70 is engaged with the internal threads 64 formed along the inner surfaces 62*a*, 62*b* of the arm portions 52*a*, 52*b* to capture the elongate member 12 within the U-shaped channel 54. In one embodiment, the set screw 70 includes a lower bearing surface 76 that engages and bears against the elongate member 12 positioned within the U-shaped channel 54 of the head portion 24 to compress the elongate member 12 against the lower arcuate bearing surface 60 defined by the transverse base portion 50.

In the illustrated embodiment, the reduced strength portion 26 of the bone anchor 20 defines a region of reduced strength 80 relative to adjacent portions 82*a*, 82*b* of the tool engaging portion 22 and the head portion 24 to provide a pre-defined fracture initiator or break zone. In one embodiment, the reduced strength portion 26 has a reduced transverse cross section relative to the adjacent portions 82*a*, 82*b* of the tool engaging portion 22 and the head portion 24, respectively, to provide the pre-defined fracture initiator or break zone. In one specific embodiment, the reduced strength portion 26 comprises an annular groove 84 extending about the longitudinal axis L and positioned between the adjacent portions 82*a*, 82*b* of the tool engaging portion 22 and the head portion 24, respectively, to define the reduced transverse cross section. In another specific embodiment, the annular groove 84 is defined by an arcuate concave surface 86 extending between the adjacent portions 82*a*, 82*b* of the tool engaging portion 22 and the head portion 24. In yet another specific embodiment, the reduced transverse cross section defined by the reduced strength portion 26 is provided by a localized reduction in material thickness t relative to the adjacent portions 82*a*, 82*b* of the tool engaging portion 22 and the head portion 24, respectively.

Figure 5:
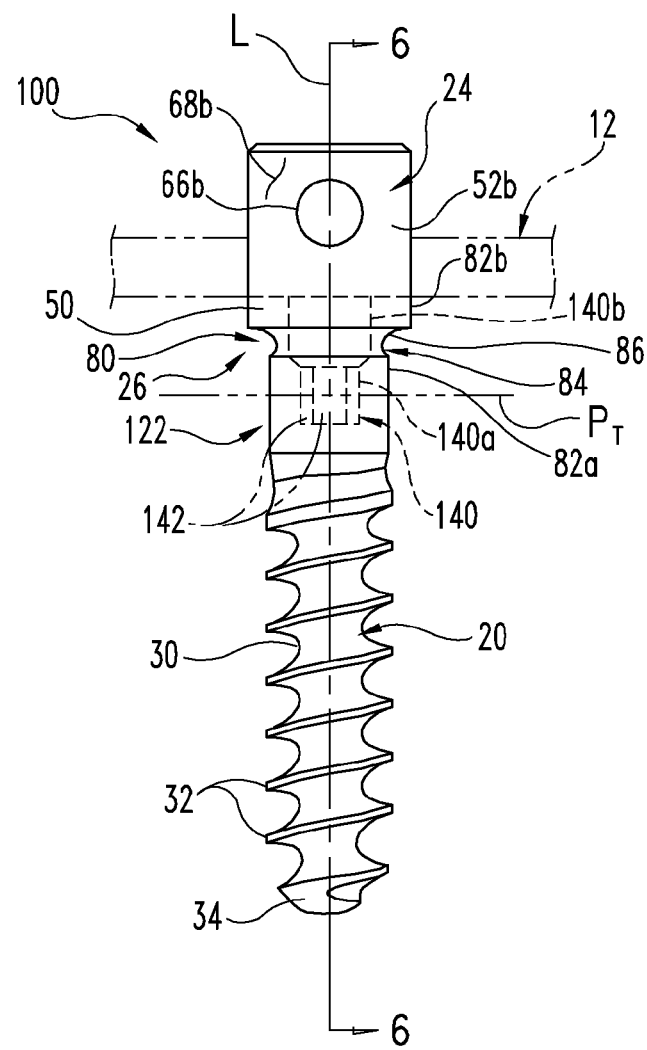
FIG. 5 is an elevational side view of another embodiment of a bone anchor for use in association with the spinal stabilization system illustrated in FIG. 1.
Figure 6:
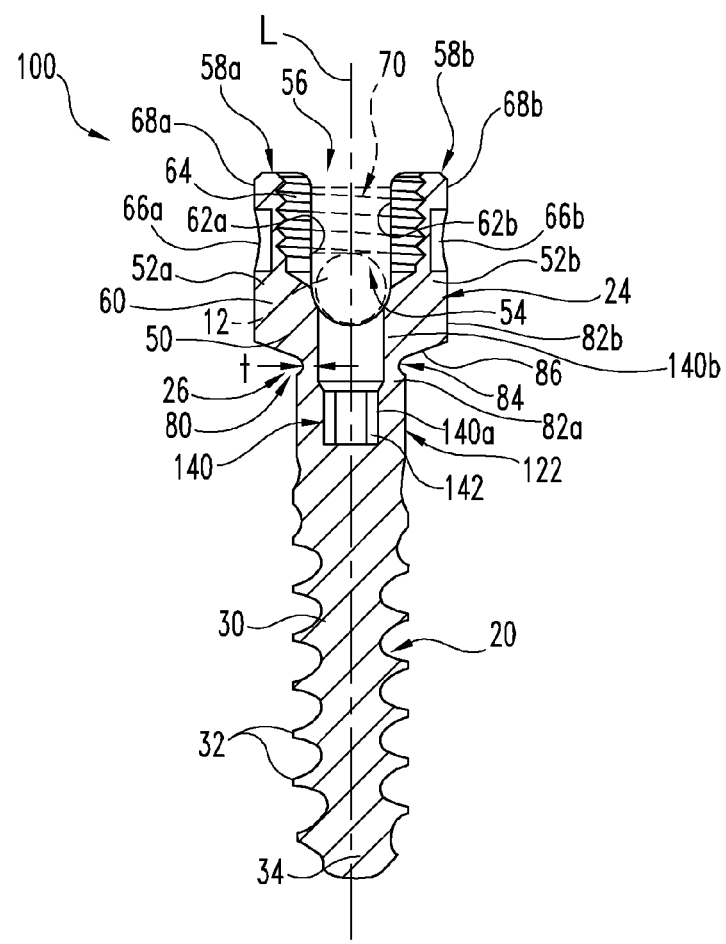
FIG. 6 is a cross-sectional view of the bone anchor illustrated in FIG. 5, as taken along line 6-6 of FIG. 5.

Referring to FIGS. 5 and 6, shown therein is a bone anchor 100 according to another form of the present invention. In the illustrated embodiment, the bone anchor 100 includes elements and features that are the same as or similar to those associated with the bone anchor 14 illustrated in FIGS. 2 and 3 and described above, with like or similar elements and features designated with corresponding reference numbers. The bone anchor 100 generally includes a bone engaging portion 20 adapted for anchoring in bone, a tool engaging portion 122 extending axially from a proximal end of the bone engaging portion 20 and sized and shaped for engagement with a bone anchor removal tool, a head portion 24 configured to receive the elongate member 12, and a reduced strength portion 26 extending between the tool engaging portion 122 and the head portion 24.

In the illustrated embodiment, the bone anchor 100 is configured as a bone screw, with the bone engaging portion 20 comprising a threaded shank 30 having a length extending along a longitudinal axis L and including external threads 32 configured for anchoring in bone, and a distal end portion 34 configured to penetrate bone. Additionally, the tool engaging portion 122 of the bone anchor 100 is configured for engagement with a bone anchor removal tool such as, for example, the bone anchor removal tool 500 illustrated in FIG. 8. As discussed below, upon removal or breakage of the head portion 24 from the remainder of the bone anchor 100, at least a portion of the tool engaging portion 122 will remain exposed above the outer bone surface $B_S$ to provide a structure for engagement by the bone anchor removal tool 500 to facilitate removal of the bone engaging portion 20 from the bone B.

In one embodiment, the tool engaging portion 122 has a non-circular inner transverse cross section taken along a transverse plane $P_T$ arranged generally perpendicular to the longitudinal axis L. The non-circular inner transverse cross section is defined by an axial passage 140 extending at least partially through the tool engaging portion 122 and arranged generally along the longitudinal axis L. In a specific embodiment, the inner periphery defined by the axial passage 140 of the tool engaging portion 122 includes a plurality of flattened surfaces 142 that provide the tool engaging portion 122 with the non-circular inner cross section. In the illustrated embodiment, the inner periphery of the axial passage 140 has a polygonal shape, and more particularly a hexagonal shape, to provide the tool engaging portion 122 with the non-circular inner cross section. However, it should be understood that other shapes and configurations of the axial passage 140 are also contemplated.

Additionally, in the illustrated embodiment, the axial passage 140 extends into communication with and intersects the U-shaped channel 54 in the head portion 24 of the bone anchor 100. Furthermore, in a specific embodiment, the lower portion 140*a* of the axial passage 140 positioned below the reduced strength portion 26 is provided with the non-circular or hexagonally-shaped inner cross section, whereas the upper portion 140*b* of the axial passage 140 positioned above the reduced strength portion 26 is provided with a generally circular inner cross section. However, other configurations of the axial passage 140 are also contemplated. Additionally, since the bone anchor removal features of the tool engaging portion 122 are internal to the tool engaging portion 122 (i.e., defined within the axial passage 140), the exterior surface of the tool engaging portion 122 may have a smooth, cylindrical configuration, or may alternatively define additional turns of the external threads 32 formed along the bone engaging portion 20. Furthermore, since the bone anchor removal features are internal to the tool engaging portion 122, the tool engaging portion 122 may be partially or fully embedded within bone B so long as the axial passage 140 remains accessible by the bone anchor removal tool 500 illustrated in FIG. 8.

In the illustrated embodiment, the head portion 24 of the bone anchor 100 is tulip-shaped and includes a transverse base portion 50 and two arm portions 52*a*, 52*b* defining a generally U-shaped channel 54 therebetween having an upper opening 56 defined between distal ends 58*a*, 58*b* of the arm portions 52*a*, 52*b* and intersecting the longitudinal axis L and sized to axially receive the elongate member 12 into the U-shaped channel 54. Additionally, the transverse base portion 50 has an arcuate or semi-circular lower bearing surface 60 extending between the opposing inner side surfaces 62*a*, 62*b* of the arm portions 52*a*, 52*b* and sized and shaped to matingly receive and engage the elongate member 12. Furthermore, in one embodiment, the transverse base portion 50 is integrally joined with the tool engaging portion 122 by the reduced strength portion 26 to provide the head portion 24 and the tool engaging portion 22 as a single unitary piece. In another embodiment, the bone engaging portion 20, the tool engaging portion 122, the head portion 24, and the reduced strength portion 26 are all formed integral with one another to provide the entire bone anchor 100 as a single unitary piece. In a further embodiment, each of the arm portions 52*a*, 52*b* define internal threads 64 formed along the opposing inner surfaces 62*a*, 62*b*, and further define recesses or indentations 66*a*, 66*b* formed in the oppositely facing outer surfaces 68*a*, 68*b*. As should be appreciated, the set screw 70 is engaged with the internal threads 64 formed along the inner surfaces 62a, 62b of the arm portions 52a, 52b to capture the elongate member 12 within the U-shaped channel 54.

In the illustrated embodiment, the reduced strength portion 26 of the bone anchor 20 defines a region of reduced strength 80 relative to adjacent portions 82a, 82b of the tool engaging portion 122 and the head portion 24, respectively, to provide a pre-defined fracture initiator or break zone. In one embodiment, the reduced strength portion 26 has a reduced transverse cross section relative to the adjacent portions 82a, 82b of the tool engaging portion 122 and the head portion 24, respectively, to provide the pre-defined fracture initiator or break zone. In one specific embodiment, the reduced strength portion 26 comprises an annular groove 84 extending about the longitudinal axis L and positioned between the adjacent portions 82a, 82b of the tool engaging portion 122 and the head portion 24 to define the reduced transverse cross section. In another specific embodiment, the annular groove 84 is defined by an arcuate concave surface 86 extending between the adjacent portions 82a, 82b of the tool engaging portion 122 and the head portion 24, respectively. In yet another specific embodiment, the reduced transverse cross section defined by the reduced strength portion 26 is provided by a localized reduction in material thickness t between the adjacent portions 82a, 82b of the tool engaging portion 122 and the head portion 24, respectively. Although the illustrated embodiment of the reduced strength portion 26 comprises an annular groove 84 extending about an exterior surface of the bone anchor 100, it should be understood that in other embodiments the annular groove may be provided along an interior surface of the bone anchor 100 such as, for example, along an interior surface extending about the axial passage 140.

As illustrated in FIG. 1 and as described above, a plurality of bone anchors 14 are initially anchored to respective vertebrae V1, V2, V3, V4 and V5. The elongate member 12 is then inserted through the upper opening 56 in the head portions 24 of the bone anchors 14 and into the U-shaped channels 54. In some instances, the U-shaped channels 54 of at least some of the bone anchors 14 are not in axial alignment with one another, and it may be necessary to apply an axial compression or reduction force onto the elongate member 12 by way of a compression or reduction instrument to reduce the elongate member 12 into the U-shaped channels 54. As should be appreciated, exertion of an axial reduction force onto the elongate member 12 to force the elongate member 12 into the U-shaped channel 54 of a bone anchor 14 may result in exertion of a lateral or transverse force onto the head portion 24 by the elongate member 12. Application of a lateral or transverse force onto the head portion 24 may in turn result in inadvertent breakage of the head portion 24 from the remainder of the bone anchor 14 at the reduced strength portion 26 defining the region of reduced strength 80. However, providing an elongate member 12 that exhibits sufficient flexibility relative to the reduced strength portion 26 of the bone anchor 14 tends to avoid or at least reduce the likelihood of breakage of the bone anchor 14 along the pre-defined fracture initiator or break zone defined by the region of reduced strength 80 when the flexible elongate member 12 is forced into the U-shaped channel 80 via an axial compression or reduction force. Once the elongate member 12 is positioned within the U-shaped channels 54 of the bone anchors 14, a closure member 16 is engaged with each of the bone anchors 14 to capture the elongate member 12 within the U-shaped channels 54 of the bone anchor 14.

In one embodiment, providing the elongate member 12 with sufficient flexibility relative to the reduced strength portions 26 of the bone anchors 14 may be accomplished via forming the elongate member 12 of a first material and the bone anchors 14 of a second material different from the first material. In one specific embodiment, the elongate member 12 is formed of a flexible, non-rigid material such as, for example, a polymeric or PEEK material, one or more superelastic metals or alloys such as, for example, nitinol, a composite material, or other flexible, non-rigid materials that would occur to one of ordinary skill in the art, and the bone anchors 14 may be formed from a metallic material such as, for example, titanium, a titanium alloy, stainless steel, or metallic alloys. In another embodiment, providing the elongate member 12 with sufficient flexibility relative to the reduced strength portions 26 of the bone anchors 14 may be accomplished via providing the elongate member 12 and/or the reduced strength portion 26 with a size, shape, configuration or material thickness that in turn provides the elongate member 12 with relatively greater flexibility relative to the reduced strength portions 26 of the bone anchors 14.

Referring now to FIG. 7, shown therein is the bone anchor 14 with the bone engaging portion 20 anchored within vertebral bone B and with the head portion 24 broken away from the remainder of the bone anchor 14. As sometimes occurs in spinal stabilization systems, bone anchors fracture or break as a result of bone screw fatigue and/or the application of excessive forces to the bone anchors. With regard to prior bone anchors, the location of the break commonly occurs below the head portion of the bone anchor and adjacent the surface of the bone where the bone engaging portion has penetrated into the bone. However, as illustrated in FIG. 7, the bone anchor 14 is provided with one or more features that cause the break to occur at a location above the outer bone surface $B_S$. In the illustrated embodiment, the bone anchor 14 is provided with a reduced strength portion 26 located just below the head portion 24 but above the outer bone surface $B_S$ so as to define a pre-defined fracture initiator or break zone located above the outer bone surface $B_S$. As a result, if forces applied to the head portion 24 via the elongate member 12 (or another element or structure) cause the head portion 24 to break away from the remainder of the bone anchor 14, the resulting fracture line F will be located above the outer bone surface $B_S$.

Additionally, with regard to prior bone anchors, the head portion of the bone anchor normally includes the structural features that serve to drive the bone engaging portion into the bone. As a result, if the head portion is broken away from the remainder of the bone anchor, the process of extracting the bone engaging portion from the bone after the head portion has broken away can be difficult and time consuming, and may require removal of a portion of the bone material adjacent the bone engaging portion which can weaken the structure of the bone. However, as illustrated in FIG. 7, the bone anchor 14 is provided with a tool engaging portion 22 that is sized and shaped for engagement with a bone anchor removal tool 400. Since the tool engaging portion 22 is located below the reduced strength portion 26 of the bone anchor 14 but is positioned at least partially above the outer bone surface $B_S$, the segment of the tool engaging portion 22 that remains above the outer bone surface $B_S$ can be easily grasped or engaged by the bone anchor removal tool 400 to facilitate removal/extraction of the bone engaging portion 20 from the bone B.

In the illustrated embodiment, the anchor removal tool 400 is configured as a wrench or socket tool including an axial drive shaft 402 and a distal bone anchor engagement portion 404 defining an axial recess or socket 406 that is sized and shaped to receive and engage the tool engaging portion 22 of the bone anchor 14. In one embodiment, the axial socket 406 has a non-circular inner transverse cross section corresponding to the non-circular outer transverse cross section of the tool engaging portion 22 of the bone anchor 14. In a specific embodiment, the inner periphery of the axial socket 406 includes a plurality of flattened surfaces 408 that correspond to the flattened surfaces 42 on the tool engaging portion 22 of the bone anchor 14. In a more specific embodiment, the inner periphery of the axial socket 406 has a polygonal shape, and more particularly a hexagonal shape, to engagingly receive the polygonal or hexagonal shape defined by the outer periphery of the tool engaging portion 22. Upon engaging receipt of the tool engaging portion 22 within the axial socket 406, rotation of the bone anchor removal tool 400 will correspondingly rotate the bone engaging portion 20 which will in turn result in removal/extraction of the bone engaging portion 20 from the bone B.

Figure 8:
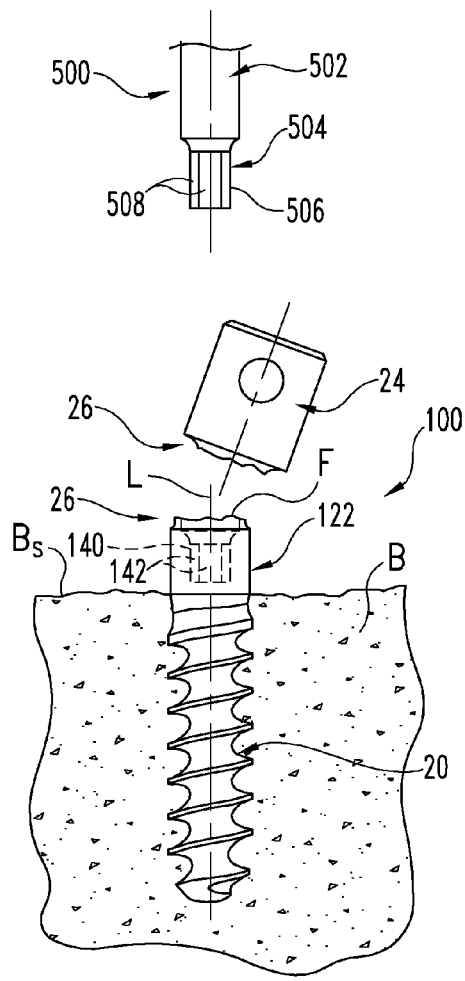
FIG. 8 is a lateral view of the bone anchor illustrated in FIG. 5 with the bone engaging portion anchored within vertebral bone and with the head portion broken away from the bone engaging portion, and a removal tool for removing the bone engaging portion of the bone anchor from the bone, and also illustrating one embodiment of a removal tool for removal of the bone engaging portion of the bone anchor from the bone.

Referring now to FIG. 8, shown therein is the bone anchor 100 with the bone engaging portion 20 anchored within vertebral bone B and with the head portion 24 broken away from the remainder of the bone anchor 100. As should be appreciated, the bone anchor 100 is provided with one or more features that cause bone anchor breakage to occur at a location above the outer bone surface $B_S$. In the illustrated embodiment, the bone anchor 100 is provided with a reduced strength portion 26 located just below the head portion 24 but above the outer bone surface $B_S$ so as to define a pre-defined fracture initiator or breakage zone located above the outer bone surface $B_S$. As a result, if forces applied to the head portion 24 via the elongate member 12 (or another element or structure) cause the head portion 24 to break away from the remainder of the bone anchor 100, the resulting fracture line F will be located above the outer bone surface $B_S$.

Additionally, the bone anchor 14 is provided with a tool engaging portion 122 that is sized and shaped for engagement with an anchor removal tool 500. Since the tool engaging portion 122 is located below the reduced strength portion 26 of the bone anchor 100 but is positioned at least partially above the outer bone surface $B_S$, the segment of the tool engaging portion 122 that remains above the outer bone surface $B_S$ can be easily engaged by the bone anchor removal tool 500 to facilitate removal/extraction of the bone engaging portion 20 of the bone anchor 100 from the bone B.

In the illustrated embodiment, the anchor removal tool 500 is configured as a driver tool including an axial drive shaft 502 and a distal bone anchor engagement portion 504 defining an axial stem 506 that is sized and shaped for receipt and engagement within the axial passage 140 defined in the tool engaging portion 122 of the bone anchor 100. In one embodiment, the axial stem 506 has a non-circular outer transverse cross section corresponding to the non-circular inner transverse cross section of the axial passage 140 in the tool engaging portion 122 of the bone anchor 100. In a specific embodiment, the outer periphery of the axial stem 506 includes a plurality of flattened surfaces 508 that correspond to the flattened surfaces 142 defined within the axial passage 140 of the tool engaging portion 122. In a more specific embodiment, the outer periphery of the axial stem 506 has a polygonal shape, and more particularly a hexagonal shape, for engaging receipt within the polygonal or hexagonal shape defined by the inner periphery of the axial passage 140 in the tool engaging portion 122. Upon engaging receipt of the axial stem 506 of the bone anchor removal tool 500 within the axial passage 140 in the tool engaging portion 122, rotation of the bone anchor removal tool 500 will correspondingly rotate the bone engaging portion 20 which will in turn result in removal/extraction of the bone engaging portion 20 from the bone B.

Figure 9:
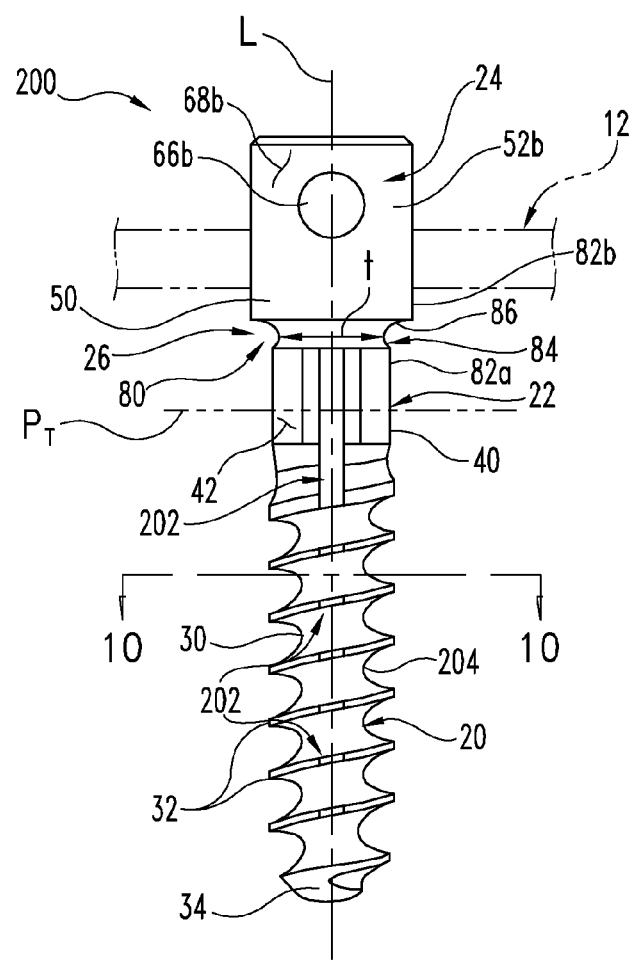
FIG. 9 is an elevational side view of another embodiment of a bone anchor for use in association with the spinal stabilization system illustrated in FIG. 1.
Figure 10:
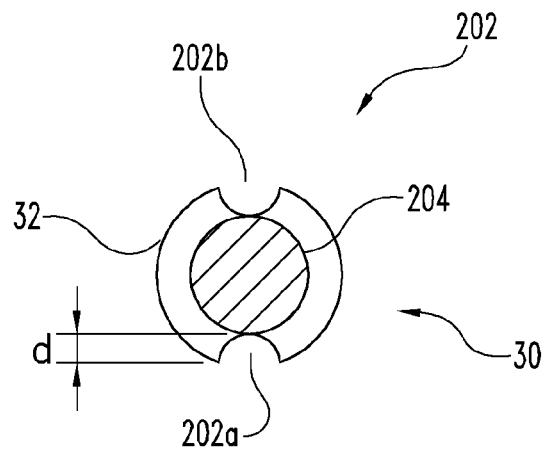
FIG. 10 is a cross-sectional view of the bone anchor illustrated in FIG. 9, as taken along line 10-10 of FIG. 9.

Referring to FIGS. 9 and 10, shown therein is a bone anchor 200 according to another form of the present invention. In the illustrated embodiment, the bone anchor 200 includes elements and features that are the same as or similar to those associated with the bone anchor 14 illustrated in FIGS. 2 and 3 and described above, with like or similar elements and features designated with corresponding reference numbers. The bone anchor 200 generally includes a bone engaging portion 20 adapted for anchoring in bone, a tool engaging portion 22 extending axially from a proximal end of the bone engaging portion 20 and sized and shaped for engagement with a bone anchor removal tool, a head portion 24 configured to receive the elongate member 12, and a reduced strength portion 26 extending between the tool engaging portion 22 and the head portion 24. In the illustrated embodiment, the bone anchor 200 is configured as a bone screw with the bone engaging portion 20 comprising a threaded shank 30 having a threaded length extending along a longitudinal axis L and including external threads 32 configured for anchoring in bone, and a distal end portion 34 configured to penetrate bone. In one embodiment, the external threads 32 are cancellous threads configured for secure anchoring in cancellous bone. In a further embodiment, the threaded length of the shank 30 is at least twice the overall height of the proximal head 24 to provide sufficient bone purchase to securely anchor the threaded shank 30 within bone. Additionally, in the illustrated embodiment, the tool engaging portion 22 of the bone anchor 200 has a hexagonally shaped outer cross section that is configured for engagement with a bone anchor removal tool such as, for example, the bone anchor removal tool 400 illustrated in FIG. 7.

In addition to the elements and features of the bone anchor 14, the bone anchor 200 also includes a plurality of axially extending recesses or grooves 202 formed in the tool engaging portion 22 and in the threaded shank 30 which circumferentially interrupt the turns of the thread 32. In the illustrated embodiment of the bone anchor 200, the threaded shank 30 includes a first series of recesses 202a formed along one side of the tool engaging portion 22 and the threaded shank 30 and generally aligned with one another in the direction of the longitudinal axis L, and a second series of recesses 202b formed along a diametrically opposite side of the tool engaging portion 22 and the threaded shank 30 (i.e., diametrically opposite the first series of recesses 202a) and generally aligned with one another in the direction of the longitudinal axis L.

In the illustrated embodiment of the bone anchor 200, the recesses 202 have a depth d that extends into the tool engaging portion 22 and into the turns of the threads 32 to a location at or adjacent the inner thread root diameter 204 of the threaded shank 30. However, it should be understood that in other embodiments, the recesses 202 could alternatively be provided with a greater depth d that extends completely through the turns of the threads and into the inner thread root diameter 204 of the threaded shank 30, or could alternatively be provided with a lesser depth d that extends partially into the turns of the threads 32 to a lesser extent than that shown in FIGS. 9 and 10 but which still circumferentially interrupts the turns of the thread 32. Additionally, in the illustrated embodiment of the bone anchor 200, the recesses 202 have a semi-circular or scallop-shaped configuration. However, other configurations of the recesses 202 are also contemplated as would occur to those of ordinary skill in the art including, for example, recesses having other types of arcuate configurations, rectangular configurations, or curvilinear configurations.

Furthermore, in the illustrated embodiment of the bone anchor 200, the recesses 202a, 202b extend along substantially the entire length of the threaded shank 30 and circumferentially interrupt each of the thread turns 32. However, other configurations are also contemplated wherein the recesses 202a, 202b extend along a lesser extent of the length of the threaded shank 30 and circumferentially interrupt only a portion of the thread turns 32. For example, in an alternative embodiment, the bone anchor 200 may be configured such that the recesses 202a, 202b extend along only the proximal portion of the threaded shank 30 and circumferentially interrupt only the proximal turns of the thread 32, including embodiments where the recesses 202a, 202b circumferentially interrupt only one or two of the proximal-most turns of the thread 32. Additionally, in the illustrated embodiment of the bone anchor 200, the recesses 202a, 202b extend into the tool engaging portion 22 of the bone anchor 200. However, in other embodiments, the recesses 202a, 202b could alternatively be confined to the threaded shank portion 30 of the bone anchor 200, or still other embodiments where the recesses 202a, 202b are confined to the tool engaging portion 22 of the bone anchor 200.

Figure 11:
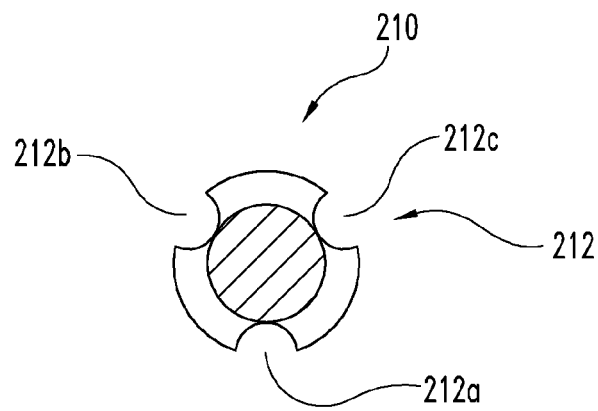
FIG. 11 is a cross-sectional view of a bone anchor according to another embodiment of the present invention.
Figure 12:
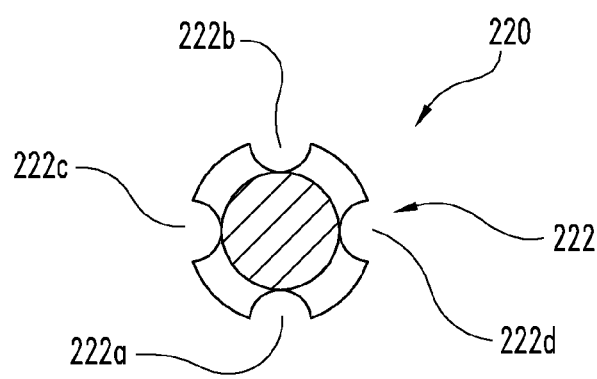
FIG. 12 is a cross-sectional view of a bone anchor according to another embodiment of the present invention.

Moreover, as illustrated in FIGS. 11 and 12, other embodiments of bone anchors are also contemplated for use in association with the present invention. For example, FIG. 11 illustrates a cross-section view of a bone anchor 210 including three series of recesses 212a, 212b and 212c that are symmetrically arranged about the threaded shank 30 and generally aligned with the longitudinal axis L. In the illustrated embodiment of the bone anchor 210, the series of recesses 212a, 212b and 212c are positioned symmetrically relative to the longitudinal axis L and are angularly offset or separated from one another by one-hundred twenty degrees. Additionally, FIG. 12 illustrates a cross-section view of a bone anchor 220 including first and second series of recesses 222a and 222b that are arranged diametrically opposite one another and generally aligned with the longitudinal axis L, and third and fourth series of recesses 222c and 222d that are arranged diametrically opposite one another and generally aligned with the longitudinal axis L. In the illustrated embodiment of the bone anchor 210, the third and fourth series of recesses 222c and 222d are positioned symmetrically relative to the longitudinal axis L and are angularly offset or separated from the first and second series of recesses 222a, 222b by ninety degrees. Other embodiments are also contemplated wherein the bone anchor 200 is provided with any number of the recesses 202 that are positioned either symmetrically or non-symmetrically relative to one another about the threaded shank 30.

Figure 13:
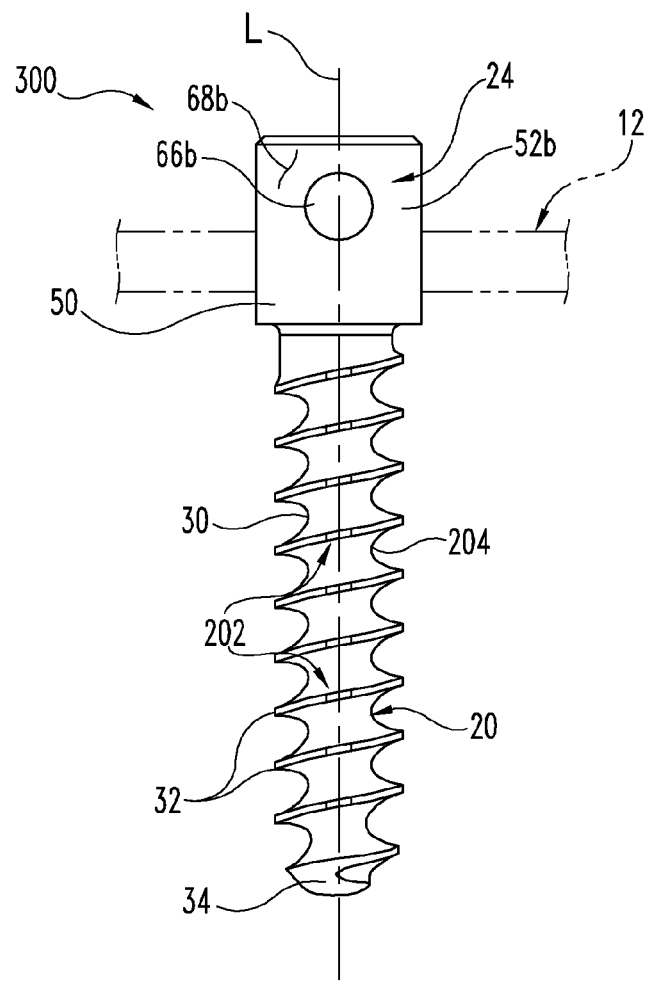
FIG. 13 is an elevational side view of another embodiment of a bone anchor for use in association with the spinal stabilization system illustrated in FIG. 1.

Referring to FIG. 13, shown therein is a bone anchor 300 according to another form of the present invention. In the illustrated embodiment, the bone anchor 300 includes elements and features that are the same as or similar to those associated with the bone anchor 200 illustrated in FIGS. 9 and 10 and described above, with like or similar elements and features designated with corresponding reference numbers. The bone anchor 300 generally includes a bone engaging portion 20 adapted for anchoring in bone and a head portion 24 configured to receive the elongate member 12. In the illustrated embodiment, the bone anchor 300 is configured as a bone screw with the bone engaging portion 20 comprising a threaded shank 30 having a threaded length extending along a longitudinal axis L and including external threads 32 configured for anchoring in bone, and a distal end portion 34 configured to penetrate bone. In one embodiment, the external threads 32 are cancellous threads configured for secure anchoring in cancellous bone. In a further embodiment, the threaded length of the shank 30 is at least twice the overall height of the proximal head 24 to provide sufficient bone purchase to securely anchor the threaded shank 30 within bone. Additionally, like the bone anchor 200, the bone anchor 300 likewise includes a series of recesses or grooves 202 formed in the threaded shank 30 and having a depth extending to or a point adjacent to the thread root diameter 204. However, unlike the bone anchor 200, the bone anchor 300 does not include a tool engaging portion 22 or a reduced strength portion 26. Instead, the bone engaging portion 20 transitions directly into the head portion 24. However, in other embodiments, the bone anchor 300 could be provided with a tool engaging portion 22 or a reduced strength portion 26, or both.

Figure 14:
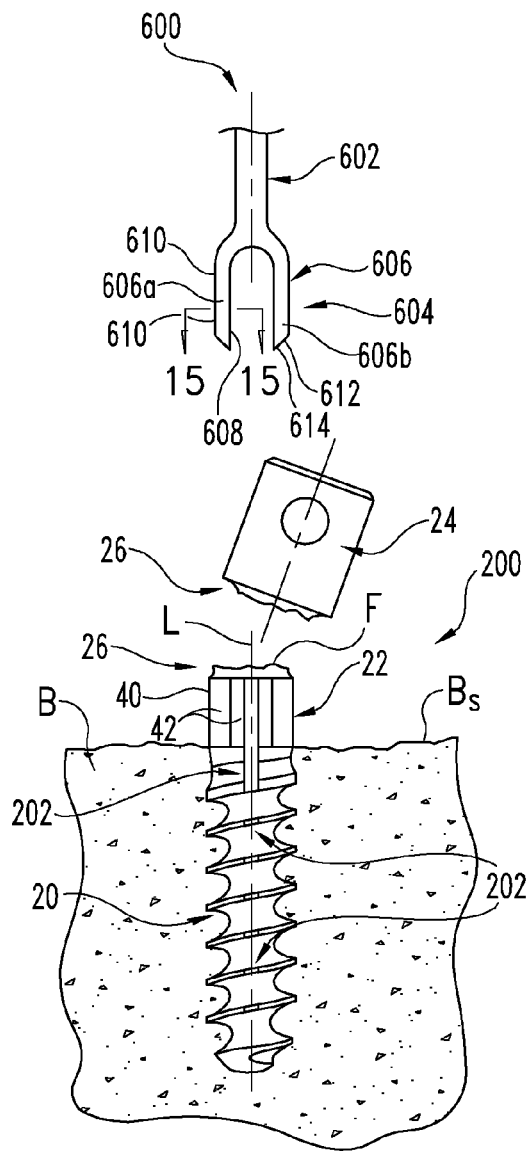
FIG. 14 is a lateral view of the bone anchor illustrated in FIG. 9 with the bone engaging portion anchored within vertebral bone and with the head portion broken away from the bone engaging portion, and also illustrating one embodiment of a removal tool for removal of the bone engaging portion of the bone anchor from the bone.

Referring now to FIG. 14, shown therein is the bone anchor 200 with the bone engaging portion 20 anchored within vertebral bone B and with the head portion 24 broken away from the remainder of the bone anchor 200. As illustrated in FIG. 14, the bone anchor 200 is provided with one or more features that tend to cause the break to occur at a location above the outer bone surface $B_S$. In the illustrated embodiment, the bone anchor 14 is provided with a reduced strength portion 26 located just below the head portion 24 but above the outer bone surface $B_S$ so as to define a pre-defined fracture initiator or break zone located above the outer bone surface $B_S$. As a result, if forces applied to the head portion 24 via the elongate member 12 (or another element or structure) cause the head portion 24 to break away from the remainder of the bone anchor 14, the resulting fracture line F will be located above the outer bone surface $B_S$. As indicated above, the bone anchor 200 is provided with a tool engaging portion 22 that is sized and shaped for engagement with a bone anchor removal tool. Since the tool engaging portion 22 is located below the reduced strength portion 26 of the bone anchor 14 but is positioned at least partially above the outer bone surface $B_S$, the segment of the tool engaging portion 22 that remains above the outer bone surface $B_S$ can be easily grasped or engaged by a bone anchor removal tool to facilitate removal/extraction of the bone engaging portion 20 from the bone B.

As illustrated in FIG. 7 and described above, a bone anchor removal tool 400 configured as a wrench or socket tool may be used to grasp onto the tool engaging portion 22 to facilitate removal of the remaining portion of the bone anchor 200 from the bone B. However, as illustrated in FIG. 14, in another embodiment, a bone anchor removal tool 600 may alternatively be provided to facilitate removal of the remaining portion of the bone anchor 200 from the bone B.

The bone anchor removal tool 600 is configured to grasp onto the tool engaging portion 22 and/or the bone engaging portion 20 of the bone anchor 200 to facilitate removal/extraction of the bone engaging portion 20 from the bone. In the illustrated embodiment, the bone anchor removal tool 600 includes an axial drive shaft 602 and a distal bone anchor engagement portion 604 including a plurality of tines or prongs 606 that are sized and shaped for receipt and engagement within the series of recesses 202 formed along the tool engaging portion 22 and/or the bone engaging portion 20 of the bone anchor 200.

Figure 15:
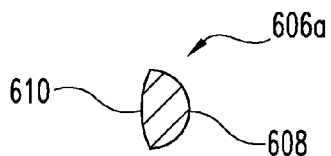
FIG. 15 is an enlarged cross-sectional view of a leg of the removal tool illustrated in FIG. 14, as taken along line 15-15 of FIG. 14.

As illustrated in FIG. 15, in one embodiment, the bone anchor removal tool 600 includes a pair of tines 606a, 606b that are arranged opposite one another, with each of the tines 606 having a semi-circular or D-shaped outer cross section including a semi-circular inwardly facing surface 608 that is generally sized and shaped for receipt and engagement within the series of semi-circular recesses 202 of the bone anchor 200, and a generally flat or arcuate-shaped outwardly facing surface 610 having a circumferential curvature that generally corresponds to the outer circumference of the major thread diameter of the threads 32 formed along the bone engaging portion 20 of the bone anchor 200. The outwardly facing surface 610 of the tines 606 preferably does not extend beyond the major thread diameter of the threads 32 when the tines 606 are received and engaged within the recesses 202 formed along the bone engaging portion 20 of the bone anchor 200. The tines 606 may be provided with an angled distal end surface 612 that tapers inwardly from the outwardly facing surface 610 toward the inwardly facing surface 608 so as to define a pointed distal end or tip 614. The angled distal end surface 612 and the pointed distal end 614 may facilitate insertion of the tines 606 into the recesses 202 in the bone engaging portion 20 of the bone anchor 200 via cutting or chiseling away of any bone in-growth material from between the thread turns 32 and from the recesses 202. Upon receipt of the tines 606 of the bone anchor removal tool 600 within the recesses 202 formed along the tool engaging portion 22 and/or the bone engaging portion 20 of the bone anchor 200, rotation of the bone anchor removal tool 600 will correspondingly rotate the bone engaging portion 20, which will in turn result in removal/extraction of the bone engaging portion 20 from the bone B.

As should be appreciated, the bone anchor removal tool 600 can be provided with any number of tines 606 that are sized, shaped and positioned for receipt and engagement within the recesses 202 formed along the tool engaging portion 22 and/or the bone engaging portion 20 of the bone anchor 200. Although the bone anchor removal tool 600 has been illustrated as including two tines 606a, 606b arranged opposite one another, it should be understood that other embodiments of the bone anchor removal tool may be provided with three or four or more tines that are arranged either symmetrically or non-symmetrically relative to the longitudinal axis of the bone anchor removal tool. Additionally, although the tines 606 have been illustrated and described as having a semi-circular or D-shaped outer cross section, other shapes and configurations of the tines 606 are also contemplated.

Figure 16:
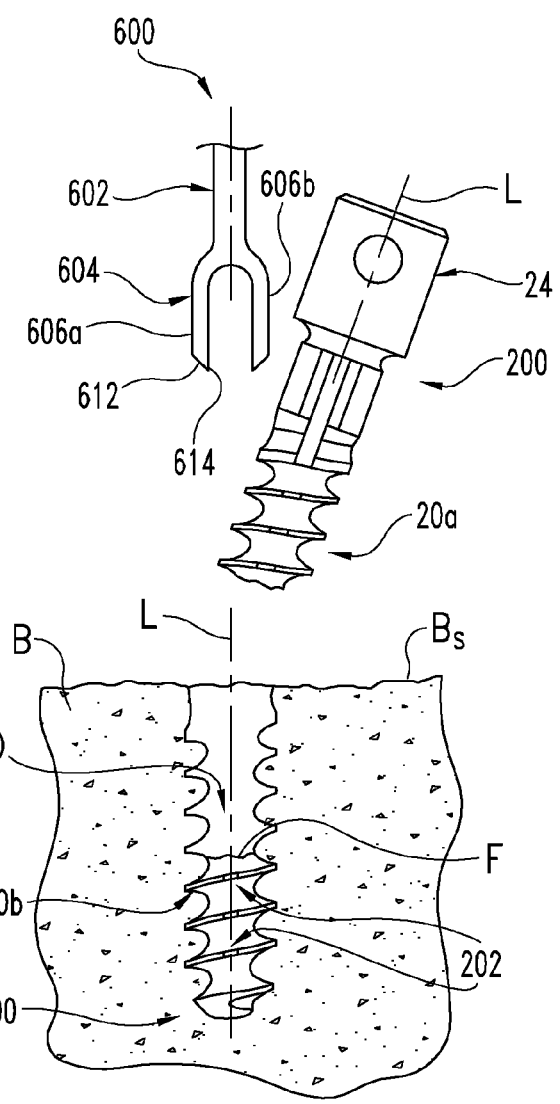
FIG. 16 is a lateral view of the bone anchor illustrated in FIG. 9 with the bone engaging portion anchored within vertebral bone and with the head portion and the proximal region of the bone engaging portion broken away from the remainder of the bone engaging portion with the fracture line positioned below the outer surface of the bone, and also illustrating the removal tool illustrated in FIG. 14 for removal of the remaining bone engaging portion of the bone anchor from the bone.

Referring now to FIG. 16, shown therein is a distal section 20b of the bone engaging portion 20 of the bone anchor 200 anchored within vertebral bone B, and with the head portion 24 and a proximal section 20a of the bone anchor 200 broken away from the distal section 20b of the bone engaging portion 20. As sometimes occurs, a force applied to the head portion 24 of the bone anchor 200 may cause the bone engaging portion 20 of the bone anchor 200 to break at a location below the outer bone surface $B_S$, thereby resulting in a fracture line F located below the outer bone surface $B_S$. In such instances, no portion of the bone anchor 200 extends outside of the bone B, and therefore can not be easily grasped by conventional bone anchor removal tools to facilitate removal of the distal section 20b of the bone engaging portion 20 from the bone B. However, since the distal section 20b of the bone anchor 200 is provided with the recesses 202, the distal bone anchor engagement portion 604 of the bone anchor removal tool 600 may be inserted through the opening O in the bone B to position the tines 606a, 606b within the recesses 202 formed along the distal section 20b of the bone engaging portion 20. Upon receipt of the tines 606a, 606b within the recesses 202 in the distal section 20b, rotation of the bone anchor removal tool 600 will correspondingly rotate the distal section 20b, which will in turn result in removal/extraction of the distal section 20b from the bone B.

As should be appreciated, the bone anchor removal tool 600 is configured for engagement within the recesses 202 formed along the tool engaging portion 22 of the bone anchor 200 in instances where the tool engaging portion 22 remains attached to the bone engaging portion 20 after the head portion 24 has broken away from the bone engaging portion 20 and the fracture line F is located above the outer bone surface $B_S$. However, as should also be appreciated, the bone anchor removal tool 600 is also configured for engagement within the recesses 202 formed along the distal section 20b of the bone engaging portion 20 of the bone anchor 200 in instances where the head portion 24 and the proximal section 20a of the bone engaging portion 20 are broken away from the distal section 20b and the fracture line F is located below the outer bone surface $B_S$.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. Any theory, mechanism of operation, proof or finding stated herein is meant to further enhance understanding of the present invention, and is not intended to make the present invention in any way dependent upon such theory, mechanism of operation, proof or finding.

It should be understood that while the use of the word preferable, preferably or preferred in the description above indicates that the feature so described may be more desirable, it nonetheless may not be necessary, and embodiments lacking the same may be contemplated as within the scope of the application, that scope being defined by the claims that follow. In reading the claims, it is intended that when words such as "a", "an", "at least one", and "at least a portion" are used, there is no intention to limit the claim to only one item unless specifically stated to the contrary in the claim. Further, when the language "at least a portion" and/or "a portion" is used, the item may include a portion and/or the entire item unless specifically stated to the contrary.

What is claimed is:

1. A bone anchor, comprising:
a bone engaging portion having a longitudinal axis and adapted for anchoring to bone;
a tool engaging portion extending axially from said bone engaging portion and sized and shaped for engagement with an anchor removal tool;
a head portion having a transverse base portion and two arm portions extending from said transverse base portion generally along the longitudinal axis to define a U-shaped channel having an opening defined between distal ends of said arm portions and intersecting the longitudinal axis and sized to axially receive an elongate member into said U-shaped channel; and
a reduced strength portion positioned below said U-shaped channel extending between said tool engaging portion and said head portion and defining a region of reduced strength relative to adjacent portions of said tool engaging portion and said head portion to provide a pre-defined fracture initiator zone.

2. The bone anchor of claim 1, wherein said tool engaging portion has a non-circular transverse cross section configured for engagement with the anchor removal tool.

3. The bone anchor of claim 2, wherein said non-circular cross section comprises a non-circular outer transverse cross section defined by an outer periphery of said tool engaging portion.

4. The bone anchor of claim 3, wherein said outer periphery of said tool engaging portion includes at least two flattened surfaces that provide said tool engaging portion with said non-circular outer cross section.

5. The bone anchor of claim 4, wherein said non-circular outer cross section is hexagonally-shaped.

6. The bone anchor of claim 2, wherein said non-circular cross section comprises a non-circular inner transverse cross section defined by an axial passage in said tool engaging portion.

7. The bone anchor of claim 6, wherein said axial passage in said tool engaging portion includes at least two flattened surfaces that provide said tool engaging portion with said non-circular inner cross section.

8. The bone anchor of claim 7, wherein said non-circular inner cross section is hexagonally-shaped.

9. The bone anchor of claim 6, wherein said axial passage extends into communication with said U-shaped channel in said head portion.

10. The bone anchor of claim 1, wherein said reduced strength portion has a reduced transverse cross section relative to said adjacent portions of said tool engaging portion and said head portion to provide said pre-defined fracture initiator zone.

11. The bone anchor of claim 10, wherein said reduced strength portion comprises an annular groove extending about the longitudinal axis and positioned between said adjacent portions of said tool engaging portion and said head portion to define said reduced transverse cross section.

12. The bone anchor of claim 10, wherein said reduced transverse cross section is defined by a localized reduction in material thickness between said adjacent portions of said tool engaging portion and said head portion.

13. The bone anchor of claim 1, wherein said transverse base portion of said head portion is integrally joined with said tool engaging portion by said reduced strength portion to provide said head portion and said tool engaging portion as a single unitary piece.

14. The bone anchor of claim 1, further comprising a set screw engaged with internal threads formed along said arm portions to capture the elongate member within said U-shaped channel.

15. The bone anchor of claim 1, wherein at least one of said bone engaging portion and said tool engaging portion includes a pluarality of grooves extending axially along the longitudinal axis, said plurality of grooves sized and shaped for engagement with an anchor removal instrument.

16. The bone anchor of claim 15, wherein said plurality of grooves extend entirely along said tool engaging portion and at least partially along said bone engaging portion.

17. The bone anchor of claim 15, wherein said bone engaging portion comprises a threaded shank defining a plurality of thread turns, said plurality of grooves circumferentially interrupting a plurality of said thread turns along at least a proximal region of said threaded shank adjacent said tool engaging portion.

18. The bone anchor of claim 17, wherein said plurality of grooves each have a semi-circular configuration.

19. A bone anchor, comprising:
a proximal head having an overall height, wherein said proximal head has a transverse base portion and two arm portions extending from a transverse base portion generally along the longitudinal axis to define a U-shaped channel having an opening defined between distal ends of said arm portions and intersecting the longitudinal axis and sized to axially receive an elongate member into a U-shaped channel;
a threaded shank having a longitudinal axis and including a plurality of thread turns adapted for anchoring to bone and extending along a threaded length of said threaded shank, said threaded length being at least twice said overall height of said proximal head;
wherein said threaded shank includes a plurality of grooves extending axially along the longitudinal axis and circumferentially interrupting at least one of said thread turns along a proximal region of said threaded shank, said plurality of grooves sized and shaped for engagement with an anchor removal instrument; and
a set screw engaged with internal threads formed along said arm portions to capture the elongate member within said U-shaped channel.

20. The bone anchor of claim 19, wherein said plurality of grooves extend along at least one half of said threaded length.

21. The bone anchor of claim 20, wherein said plurality of grooves extend substantially entirely along said threaded length.

22. The bone anchor of claim 19, wherein said plurality of grooves includes a first groove formed along a first side of said threaded shank, and a second groove formed along an opposite second side of said threaded shank and arranged diametrically opposite said first groove.

23. The bone anchor of claim 19, wherein said plurality of grooves includes at least three grooves positioned symmetrically about said threaded shank.

24. The bone anchor of claim 19, wherein said plurality of grooves includes four grooves positioned symmetrically about said threaded shank.

25. The bone anchor of claim 19, wherein said plurality of grooves have a depth that terminates at a location adjacent a minor thread diameter of said threaded shank.

26. The bone anchor of claim 19, wherein said plurality of grooves each have a semi-circular configuration.

27. The bone anchor of claim 19 further comprising a reduced strength portion positioned between said proximal head and said threaded shank and defining a region of reduced strength relative to adjacent portions of said proximal head and said threaded shank to provide a pre-defined fracture initiator zone.

28. A bone anchor, comprising:
a bone engaging portion having a longitudinal axis and adapted for anchoring to bone;
a tool engaging portion extending axially from said bone engaging portion and sized and shaped for engagement with an anchor removal tool;
a head portion having a transverse base portion and two arm portions extending from said transverse base portion generally along the longitudinal axis to define a U-shaped channel having an opening defined between distal ends of said arm portions and intersecting the longitudinal axis and sized to axially receive an elongate member into said U-shaped channel;
wherein at least one of said bone engaging portion and said tool engaging portion includes a plurality of grooves extending axially along the longitudinal axis, and entirely along said tool engaging portion and at least partially along said bone engaging portion, and wherein said plurality of grooves sized and shaped for engagement with an anchor removal instrument; and
a reduced strength portion positioned below said U-shaped channel extending between said tool engaging portion and said head portion and defining a region of reduced strength relative to adjacent portions of said tool engaging portion and said head portion to provide a pre-defined fracture initiator zone.

* * * * *